United States Patent
Seavey et al.

(10) Patent No.: US 10,543,030 B2
(45) Date of Patent: Jan. 28, 2020

(54) SURGICAL INSTRUMENT AND METHOD FOR USE IN SIZING FIXATION IMPLANTS

(71) Applicant: Howmedica Osteonics Corp., Mahwah, NJ (US)

(72) Inventors: Jeffrey F. Seavey, Houston, TX (US); Lance N. Terrill, League City, TX (US); Kaitlin Haymaker, Tomball, TX (US)

(73) Assignee: Howmedica Osteonics Corp., Mahwah, NJ (US)

( * ) Notice: Subject to any disclaimer, the term of this patent is extended or adjusted under 35 U.S.C. 154(b) by 334 days.

(21) Appl. No.: 15/611,504

(22) Filed: Jun. 1, 2017

(65) Prior Publication Data

US 2018/0344375 A1 Dec. 6, 2018

(51) Int. Cl.
| | | |
|---|---|---|
| *A61B 17/58* | (2006.01) | |
| *A61B 17/56* | (2006.01) | |
| *A61B 17/064* | (2006.01) | |
| *A61B 17/84* | (2006.01) | |
| *A61F 2/30* | (2006.01) | |
| *A61B 17/88* | (2006.01) | |
| *A61B 90/00* | (2016.01) | |
| *A61B 17/02* | (2006.01) | |
| *A61B 50/30* | (2016.01) | |

(52) U.S. Cl.
CPC .......... *A61B 17/88* (2013.01); *A61B 17/0206* (2013.01); *A61B 90/06* (2016.02); *A61B 17/0642* (2013.01); *A61B 50/30* (2016.02)

(58) Field of Classification Search
CPC combination set(s) only.
See application file for complete search history.

(56) References Cited

U.S. PATENT DOCUMENTS

| | | | |
|---|---|---|---|
| D669,985 S | 10/2012 | Cheney et al. | |
| 8,584,853 B2 | 11/2013 | Knight et al. | |
| 2013/0213843 A1 | 8/2013 | Knight et al. | |
| 2014/0014548 A1 | 1/2014 | Knight et al. | |
| 2015/0108024 A1 | 4/2015 | Knight et al. | |
| 2017/0296174 A1* | 10/2017 | Wahl | A61B 50/33 |

OTHER PUBLICATIONS

S TA P i X™ Superelastic Nitinol Staple Fixation, Instratek, Apr. 9, 2015, 12 pages.

* cited by examiner

*Primary Examiner* — Sameh R Boles
(74) *Attorney, Agent, or Firm* — Lerner, David, Littenberg, Krumholz & Mentlik, LLP

(57) ABSTRACT

A surgical instrument for use in sizing a bone staple implant for implantation into a patient's bone is disclosed. The surgical instrument includes an elongated body having a first longitudinal end and a second longitudinal end. A first sizing plate is attached to and extending outwardly from the first longitudinal end, and a second sizing plate is attached to and extending outwardly from the second longitudinal end. The first sizing plate includes a first visible marking that identifies a width of a first bone staple implant, and the second sizing plate includes a second visible marking that identifies a width of a second bone staple implant. A system and a method for sizing a bone staple implant for implantation into a patient's bone are also disclosed.

19 Claims, 7 Drawing Sheets

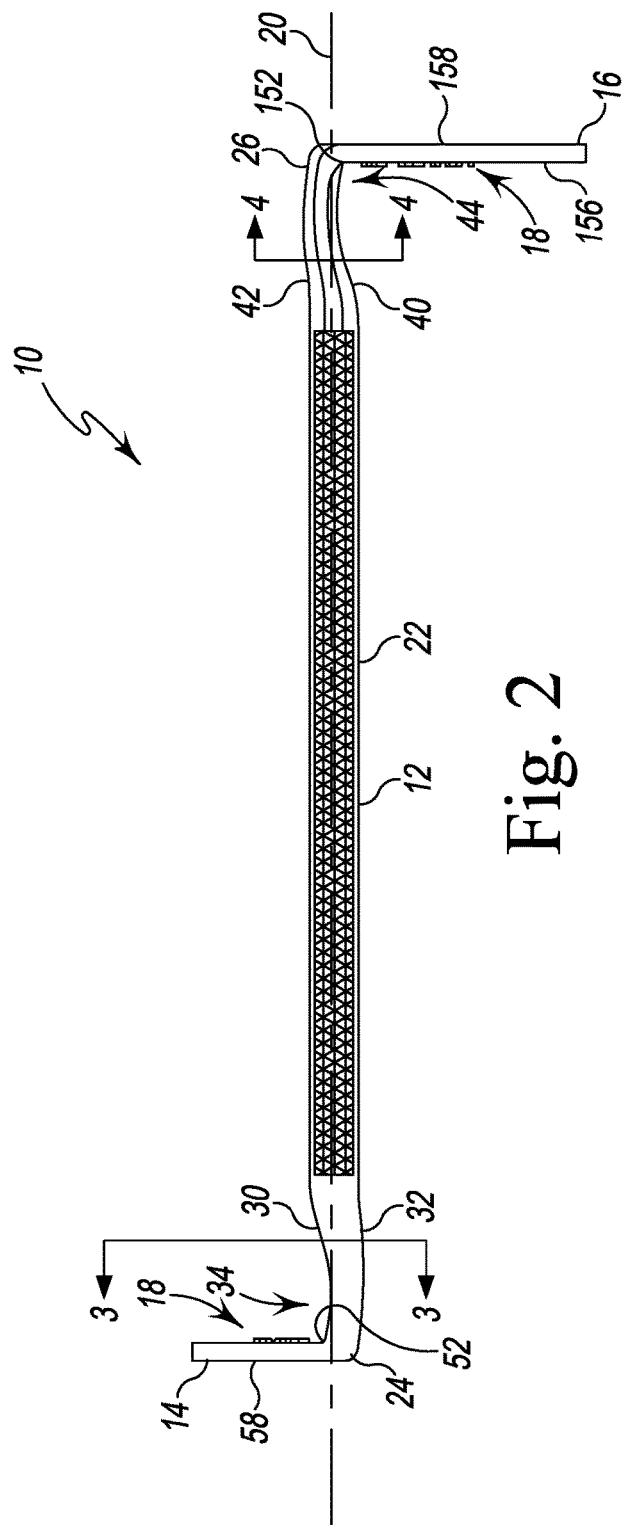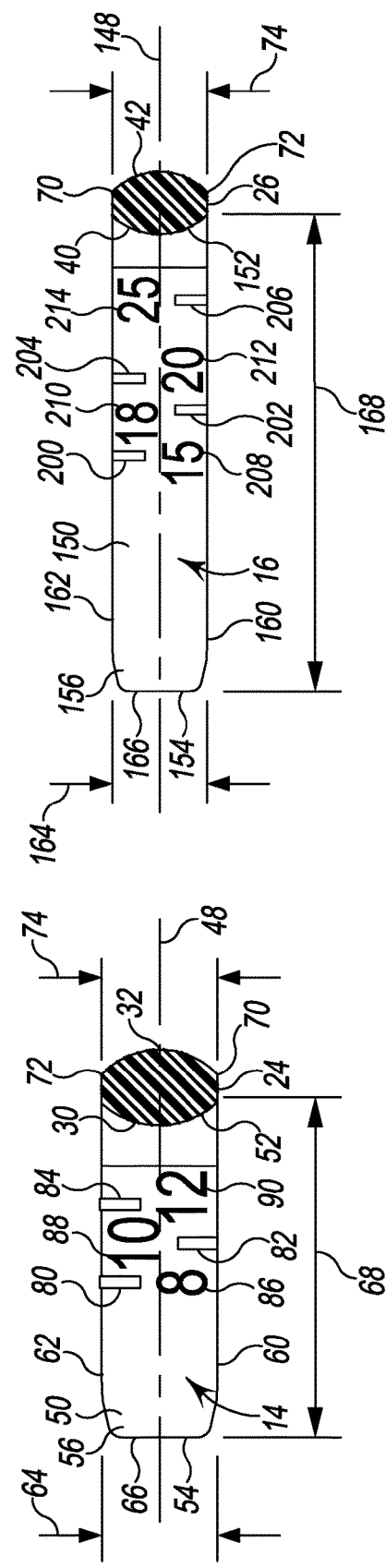

SURGICAL INSTRUMENT AND METHOD FOR USE IN SIZING FIXATION IMPLANTS

TECHNICAL FIELD

The present disclosure relates generally to instruments for use in a surgical procedure, and, more specifically, to surgical instruments for use in implanting fixation implant devices into a patient.

BACKGROUND

Repair of bones often involves the use of fixation devices to secure the bony anatomy together during the healing process. There are many forms of bone fixation devices including intramedullary devices, pins, screws, plates, and staple implants. These fixation devices may be formed from a shape memory material, such as nitinol, which creates compression that can augment healing.

Typically, fixation devices are provided in kits with the surgical instruments used to prepare the bones to receive the fixation devices. Those surgical instruments include, for example, an inserter tool that may be used to control and position the fixation device for implantation, the drill guide and drill bit for use in preparing the patient's bone, locating pins, and a tamp. One exemplary kit is the Instratek STAPiX™ system, which is commercially available from Stryker.

Various methods and instruments have been developed for use in a procedure to implant a fixation device into a patients. Methods and instruments are described in U.S. Patent App. Pub. Nos. 2015/0108024, US2013/0213843, and US2014/0014548; and U.S. Pat. Nos. D669985, 8,584,853.

SUMMARY

According to one aspect of the disclosure, a surgical instrument that is designed to assist a user in sizing a bone staple implant or other fixation device in a surgical procedure is disclosed. The surgical instrument is a one-piece tool that includes a pair of sizing plates. Each plate includes at least one visible mark that correlates to a bone staple implant size. In other words, each visible mark identifies a bone staple implant of a particular size. The surgical instrument may be included in an instrument system for using the surgical procedure.

In some embodiments, the instrument system comprises a plurality of bone staple implants configured to be implanted into a patient's bone. Each bone staple implant includes a base extending along a longitudinal axis and a pair of arms extending outwardly from the base. The pair of arms are movable to an implantation position in which the arms of each bone staple implant are spaced apart when in the implantation position such that a width is defined between a tip of each arm. The system also comprises the surgical instrument, which includes an elongated body having a first longitudinal end and a second longitudinal end, a first sizing plate attached to and extending outwardly from the first longitudinal end, and a second sizing plate attached to and extending outwardly from the second longitudinal end. The first sizing plate includes a first visible marking that identifies the width of a first bone staple implant of the plurality of bone staple implants, and The second sizing plate includes a second visible marking that identifies the width of a second bone staple implant of the plurality of bone staple implants. In some embodiments, the width of each bone staple implant correlates to the size of the bone staple implant.

In some embodiments, the first sizing plate may extend from the first longitudinal end of the surgical instrument to a distal tip, and a first distance may be defined between the distal tip and the first visible marking. The first distance may be equal to the width of the first bone staple implant. Additionally, in some embodiments, the second sizing plate may extend from the second longitudinal end of the surgical instrument to a distal tip, and a second distance may be defined between the distal tip of the second sizing plate and the second visible marking. The second distance may be equal to the width of the second bone staple implant.

In some embodiments, the first visible marking may be one of a plurality of visible markings of the first sizing plate. Each visible marking of the first sizing plate may identify the width of a different bone staple implant of the plurality of bone staple implants. Additionally, in some embodiments, the second visible marking may be one of a plurality of visible markings of the second sizing plate. Each visible marking of the second sizing plate may identify the width of a different bone staple implant of the plurality of bone staple implants.

In some embodiments, the first sizing plate may extend away from the elongated body in a first direction, and the second sizing plate may extend away from the elongated body in a second direction opposite the first direction.

In some embodiments, the instrument system may also comprise an inserter tool having a pair of jaws sized to engage the base of a bone staple implant of the plurality of bone staple implants.

In some embodiments, the longitudinal ends of the elongated body may be configured to retract the patient's tissue surrounding the patient's bone. Additionally, in some embodiments, the elongated body may have a proximal surface that is positioned opposite the first sizing plate and is configured to retract the patient's tissue surrounding the patient's bone.

In some embodiments, the first sizing plate may extend away from the elongated body along a longitudinal axis to a distal tip. The first sizing plate may have a plate thickness along an axis that is orthogonal to the longitudinal axis. The proximal surface of the elongated body may define a thickness of the elongated body that is equal to the plate thickness. Additionally, in some embodiments, the plate thickness of the first sizing plate may be constant along its longitudinal axis between the elongated body and the distal tip.

In some embodiments, the elongated body may have a proximal surface that is positioned opposite the second sizing plate and is configured to retract the patient's tissue surrounding the patient's bone. Additionally, in some embodiments, the second sizing plate may extend away from the elongated body along a longitudinal axis to a distal tip. The second sizing plate may have a plate thickness along an axis that is orthogonal to the longitudinal axis. The proximal surface of the elongated body may define a thickness of the elongated body that is equal to the plate thickness. In some embodiments, the plate thickness of the second sizing plate may be constant along its longitudinal axis between the elongated body and the distal tip.

According to another aspect, a surgical instrument for use in sizing a bone staple implant for implantation into a patient's bone is disclosed. The surgical instrument comprises an elongated body having a first longitudinal end and a second longitudinal end. The first longitudinal end and the second longitudinal end are configured to retract the patient's tissue surrounding the patient's bone. The surgical instrument also comprises a first sizing plate attached to and extending outwardly from the first longitudinal end, and a second sizing plate attached to and extending outwardly from the second longitudinal end. The first sizing plate includes a first visible marking that identifies a width of a first bone staple implant, and the second sizing plate includes a second visible marking that identifies a width of a second bone staple implant.

According to another aspect, a method for sizing a bone staple implant for implantation into a patient's bone. The method comprises inserting a first end of a surgical instrument into an incision in a patient's tissue, engaging the first end of the surgical instrument with the patient's tissue to retract the patient's tissue and expand the incision, positioning a sizing plate extending from the first end of the surgical instrument over a fracture in the patient's bone or osteotomy, locating a visible marking on the sizing plate that identifies a size of bone staple implant, and selecting the bone staple implant based on the visible marking.

In some embodiments, locating the visible marking on the sizing plate that identifies a width of a bone staple implant may include locating one visible marking of a plurality of visible markings. Each visible marking may identify a width of a different bone staple implant. In some embodiments, the width of each bone staple implant correlates to the size of each bone staple implant.

In some embodiments, locating the visible marking on the sizing plate that identifies a width of a bone staple implant may include moving the sizing plate extending from the first end of the surgical instrument away a fracture in the patient's bone, positioning a second sizing plate extending from a second end of the surgical instrument over the fracture in the patient's bone, and locating a visible marking on the second sizing plate that identifies a width of a bone staple implant.

BRIEF DESCRIPTION OF THE DRAWINGS

The detailed description particularly refers to the following figures, in which:

FIG. 2 is a side elevation view of the surgical instrument of FIG. 1;

FIG. 3 is a partial cross-sectional plan view of the surgical instrument of FIGS. 1 and 2 taken along the line 3-3 in FIG. 2;

FIG. 4 is a partial cross-sectional plan view of the surgical instrument of FIGS. 1 and 2 taken along the line 4-4 in FIG. 2;

DETAILED DESCRIPTION OF THE DRAWINGS

Figure 1:
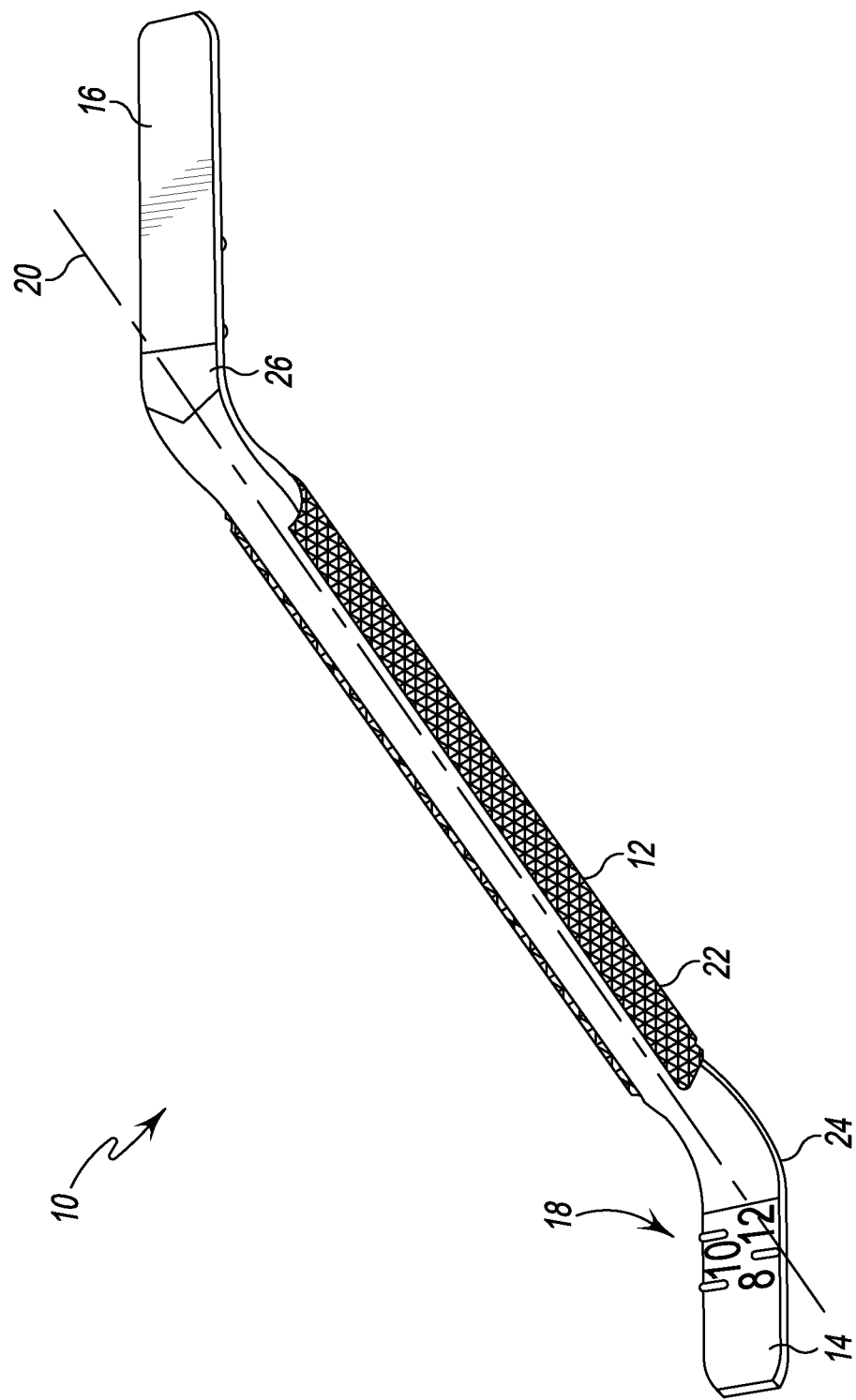
FIG. 1 is a perspective view of a surgical instrument for use in sizing a fixation device.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIG. 1, a surgical instrument 10 for use in sizing a bone staple implant or other fixation device is shown. The surgical instrument 10 includes an elongated body 12 and a pair of sizing plates 14, 16. As described in greater detail below, each of the sizing plates 14, 16 includes a plurality of visible markings 18 that correlate to and identify a size of bone staple implant such that the instrument 10 may be used to size and select a bone staple implant for use with a particular patient.

In the illustrative embodiment, the surgical instrument 10 is formed as a single, monolithic component. It should be appreciated that in other embodiments it may be formed from multiple pieces that are later assembled into a single instrument. The surgical instrument is also illustratively formed from injection-molded plastic such as polyethylene that is suitable for use with a human patient. The instrument may be formed in other embodiments from an implant-grade stainless steel or other suitable metallic material.

The elongated body 12 extends along a longitudinal axis 20 and includes a central shaft 22 that is configured to be gripped by a surgeon or other user to manipulate the instrument 10. As shown in FIG. 1, the outer surface of the shaft 22 is knurled to provide a grip for the user. The central shaft 22 extends along the longitudinal axis 20 between a pair of longitudinal ends 24, 26. In the illustrative embodiment, the sizing plate 14 is attached to and extends outwardly from the longitudinal end 24, and the sizing plate 16 is attached to and extends outwardly from the opposite longitudinal end 26.

Referring now to FIG. 2, the plates 14, 16 extend in opposite directions away from the elongated body 12. It should be appreciated that in other embodiments the sizing plates may extend in the same direction or in other directions relative to the elongated body 12. In the illustrative embodiment, the sizing plates 14, 16 extend orthogonal to the longitudinal axis 20 of the elongated body 12. In other embodiments, the sizing plates may extend transversely relative to the longitudinal axis 20 but not orthogonal to it.

The longitudinal end 24 of the elongated body 12 has an inner surface 30 that faces in the direction of the plate 14 and an opposite outer surface 32 that faces away from the plate 14. When viewed in elevation as shown in FIG. 2, the inner surface 30 and the outer surface 32 are curved, and the inner surface 30 defines a depression 34 that is positioned adjacent to the sizing plate 14. Similarly, the longitudinal and 26 of the elongated body 12 has an inner surface 40 that faces in the direction of the plate 16 and opposite outer surface 32 that faces away from the plate 16. When viewed in elevation as shown in FIG. 2, the inner surface 40 and the outer surface 42 are also curved, and the inner surface 40 defines a depression 44 that is positioned adjacent to the sizing plate 16.

Referring now to FIG. 3, the sizing plate 14 extends outwardly from the elongated body 12 along a longitudinal axis 48. The sizing plate 14 includes a flange 50 that extends along the axis 48 from an edge 52 attached to the inner surface 30 of the elongated body 12 to a distal tip 54. In the illustrative embodiment, the flange 50 has a substantially planar top surface 56 that faces the depression 34 defined in the elongated body 12. The flange 50 also includes a substantially planar bottom surface 58 (see FIG. 2) that is positioned opposite the top surface 56. A pair of sidewalls 60, 62 extends between the surfaces 56, 58. As shown in FIG. 3, the sizing plate 14 has a thickness 64 defined between the sidewalls 60, 62 along a line extending orthogonal to the longitudinal axis 48 of the plate 14. In the illustrative embodiment, the thickness 64 is constant between the distal tip 54 and the edge 52. It should be appreciated that in other embodiments the thickness may change; for example, the sizing plate 14 may taper between the edge 52 and the distal tip 54.

The distal tip 54 is slightly narrower than the rest of the flange 50. The distal tip 54 includes a planar end wall 66 that extends between the top surface 56 and the bottom surface 58. In the illustrative embodiment, the distal tip 54 is a blunt tip. It should be appreciated that in other embodiments the distal tip 54 may narrow to a relatively sharp point. As shown in FIG. 3, the sizing plate 14 extends a length 68 from the elongated body 12. The length 68 is defined in the illustrative embodiment between the edge 52 and the planar end wall 66.

The outer surface 32 (and hence the longitudinal end 24) of the elongated body 12 is configured to engage and retract a patient's tissue. As shown in FIG. 3, the outer surface 32 of the elongated body 12 extends between a pair of edges 70, 72. In the illustrative embodiment, the outer surface 32 is a convex curved surface when viewed in cross-section as shown in FIG. 3. The curved surface 32 allows the elongated body 12 to engage the patient's tissue to retract the tissue and enlarge an incision without cutting or tearing the tissue. It should be appreciated that in other embodiments the outer surface 32 may be substantially planar or have another cross-sectional shape. The outer surface 32 defines a thickness 74 of the elongated body 12 at the longitudinal end 24. In the illustrative embodiment, the thickness 74 is equal to the thickness 64 of the sizing plate 14.

As described above, the sizing plate 14 includes a plurality of visible markings 18 that correlate to and identify a size of bone staple implant such that the instrument 10 may be used to size and select a bone staple implant for use with a particular patient. In the illustrative embodiment, the visible markings 18 are arranged on the planar top surface 56 of the sizing plate 14. The markings 18 include raised tabs 80, 82, 84, which extend outwardly from the planar top surface 56 and may be used to identify a different bone staple implant. As shown in FIG. 3, the markings 18 also include numerical indicators 86, 88, 90, which correspond to each tab and correlate to sizes of bone staple implants. In other embodiments, the numerical indicators may be omitted. It should be appreciated that in other embodiments the visible markings may include slots, holes, etchings, dyes, or other visible indicia on the surface 56 to identify a different bone staple implant.

Each of the raised tabs 80, 82, 84 extends orthogonal to the longitudinal axis 48 of the sizing plate 14, substantially parallel to the planar end wall 66 of the sizing plate 14. A first distance, which extends parallel to the longitudinal axis 48, is defined between the tab 80 and the planar end wall 66. In the illustrative embodiment, the first distance is equal to a width of a bone staple implant when the bone staple implant is in its implantation position (described in greater detail below). A second distance, which also extends parallel to the longitudinal axis 48, is defined between the tab 82 and the planar end wall 66. In the illustrative embodiment, the second distance is equal to a width of a second bone staple implant when the second bone staple implant is in its implantation position. A third distance, which also extends parallel to the longitudinal axis 48, is defined between the tab 84 and the planar end wall 66. In the illustrative embodiment, the third distance is equal to a width of a third bone staple implant when the third bone staple implant is in its implantation position.

As described above, the instrument 10 has another sizing plate 16 that is positioned at its opposite longitudinal end 26. In the illustrative embodiment, the general configuration of the sizing plate 16 matches the configuration of the sizing plate 14. Like the sizing plate 14, the sizing plate 16 includes a plurality of visible markings 18 that correlate to and identify a size of bone staple implant such that the instrument 10 may be used to size and select a bone staple implant for use with a particular patient. In the illustrative embodiment, however, the visible markings 18 on the sizing plate 16 (including raised tabs 200, 202, 204, 206) identify bone staple implants that are larger than the bone staple implants identified or correlated with the raised tabs 80, 82, 84 of the sizing plate 14. As shown in FIG. 4, the sizing plate 16 is therefore longer than the sizing plate 14 and extends a length 168 that is greater than the length 68 of the sizing plate 14.

The specific configuration of the sizing plate 16 will now be described in greater detail. The sizing plate 16 extends outwardly from the elongated body 12 along a longitudinal axis 148. The sizing plate 14 includes a flange 150 that extends along the axis 148 from an edge 152 attached to the inner surface 40 of the elongated body 12 to a distal tip 154. In the illustrative embodiment, the flange 150 has a substantially planar top surface 156 that faces the depression 44 defined in the elongated body 12. The flange 150 also includes a substantially planar bottom surface 158 (see FIG. 2) that is positioned opposite the top surface 156. A pair of sidewalls 60, 62 extends between the surfaces 156, 158. As shown in FIG. 4, the sizing plate 16 has a thickness 164 defined between the sidewalls 160, 162 along a line extending orthogonal to the longitudinal axis 148 of the plate 16. In the illustrative embodiment, the thickness 164 is constant between the distal tip 154 and the edge 152. It should be appreciated that in other embodiments the thickness may change; for example, the sizing plate 16 may taper between the edge 152 and the distal tip 154.

The distal tip 154 is slightly narrower than the rest of the flange 150. The distal tip 154 includes a planar end wall 166 that extends between the top surface 156 and the bottom surface 158. In the illustrative embodiment, the distal tip 154 is a blunt tip. It should be appreciated that in other embodiments the distal tip 154 may narrow to a relatively sharp point. As shown in FIG. 4, the sizing plate 16 extends a length 168 from the elongated body 12. The length 168 is defined in the illustrative embodiment between the edge 152 and the planar end wall 166. As described above, the length 168 is greater than the length 68 of the sizing plate 14.

The outer surface 42 (and hence the longitudinal end 24) of the elongated body 12 is configured to engage and retract a patient's tissue. As shown in FIG. 4, the outer surface 42 of the elongated body 12 extends between the pair of edges 70, 72. In the illustrative embodiment, the outer surface 42 is a convex curved surface when viewed in cross-section as shown in FIG. 4. The curved surface 42 allows the elongated body 12 to engage the patient's tissue to retract the tissue and enlarge an incision without cutting or tearing the tissue. It should be appreciated that in other embodiments the outer surface 42 may be substantially planar or have another cross-sectional shape. The outer surface 42 defines a thickness 74 of the elongated body 12 at the longitudinal end 26.

In the illustrative embodiment, the thickness 74 is equal to the thickness 164 of the sizing plate 16.

As described above, the sizing plate 16 includes a plurality of visible markings 18 that correlate to and identify a size of bone staple implant such that the instrument 10 may be used to size and select a bone staple implant for use with a particular patient. In the illustrative embodiment, the visible markings 18 are arranged on the planar top surface 156 of the sizing plate 16. The markings 18 include raised tabs 200, 202, 204, 206, which extend outwardly from the planar top surface 156 and may be used to identify a different bone staple implant. As shown in FIG. 4, the markings 18 also include numerical indicators 208, 210, 212, 214, which correspond to each tab and correlate to sizes of bone staple implants. In other embodiments, the numerical indicators may be omitted. It should be appreciated that in other embodiments the visible markings may include slots, holes, etchings, dyes, or other visible indicia on the surface 156 to identify a different bone staple implant.

Each of the raised tabs 200, 202, 204, 206 extends orthogonal to the longitudinal axis 148 of the sizing plate 16, substantially parallel to the planar end wall 166 of the sizing plate 16. Like the tabs 80, 82, 84 of the sizing plate 14, which are positioned first, second, and third distances, respectively, from the planar end wall 66 of the sizing plate 14, each of the tabs 200, 202, 204, 206 is positioned a different distance from the end wall 166 of the sizing plate 16.

As shown in FIG. 4, a fourth distance, which extends parallel to the longitudinal axis 148, is defined between the tab 200 and the planar end wall 166. In the illustrative embodiment, the fourth distance is equal to a width of a fourth bone staple implant when the bone staple implant is in its implantation position. A fifth distance, which also extends parallel to the longitudinal axis 148, is defined between the tab 202 and the planar end wall 66. In the illustrative embodiment, the fifth distance is equal to a width of a fifth bone staple implant when the fifth bone staple implant is in its implantation position. A sixth distance, which also extends parallel to the longitudinal axis 48, is defined between the tab 204 and the planar end wall 66. In the illustrative embodiment, the sixth distance is equal to a width of a sixth bone staple implant when the sixth bone staple implant is in its implantation position. A seventh distance, which also extends parallel to the longitudinal axis 48, is defined between the tab 206 and the planar end wall 66. In the illustrative embodiment, the seventh distance is equal to a width of a sixth bone staple implant when the sixth bone staple implant is in its implantation position.

Although the instrument 10 includes visible markings that identify seven different bone staple implant sizes (specifically, 8 millimeters (mm), 10 mm, 12 mm, 15 mm, 18 mm, 20 mm, and 25 mm, as indicated by indicators 86, 88, 90, 208, 210, 212, 214, respectively), it should be appreciated that the instrument 10 may include additional markings to identify other bone staple implant sizes. In other embodiments, the instrument 10 may include fewer markings and thereby identify fewer bone staple implants.

Figure 5:
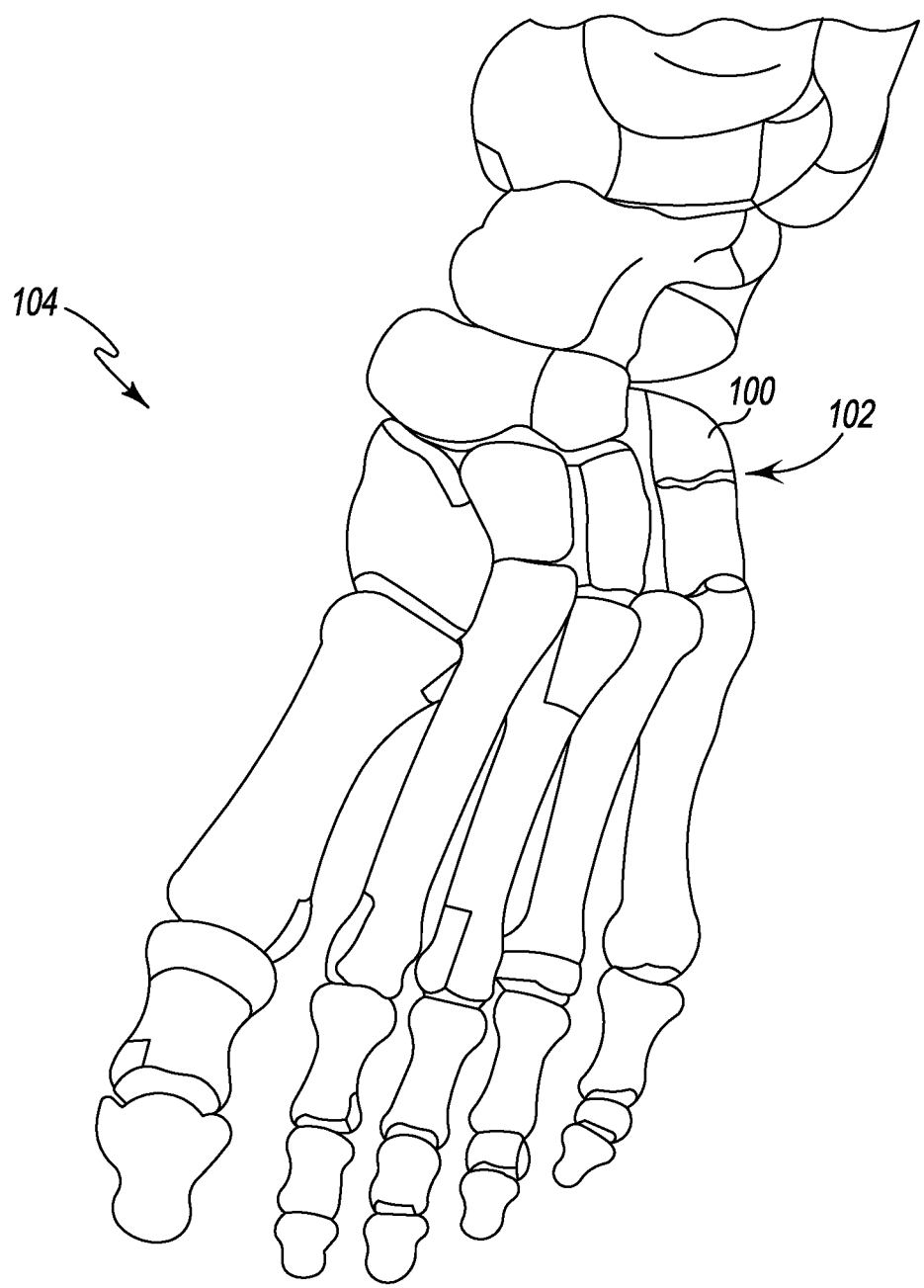
FIG. 5 is a perspective view of a patient's bone.

Referring now to FIG. 5, the surgical instrument 10 may be used to size a bone staple implant for implantation in a patient's bone 100. In the illustrative embodiment, the procedure is a fracture repair, but it should be understood the that instrument may be used in other procedures such as, for example, bone osteotomies and arthrodesis procedures. As shown in FIG. 5, the fracture 102 is formed in the bone 100 of the patient's foot 104. The surgeon may begin the procedure by forming an incision 106 (see FIG. 7) in the patient's soft tissue 108 in the area of the fracture 102.

Figure 6:
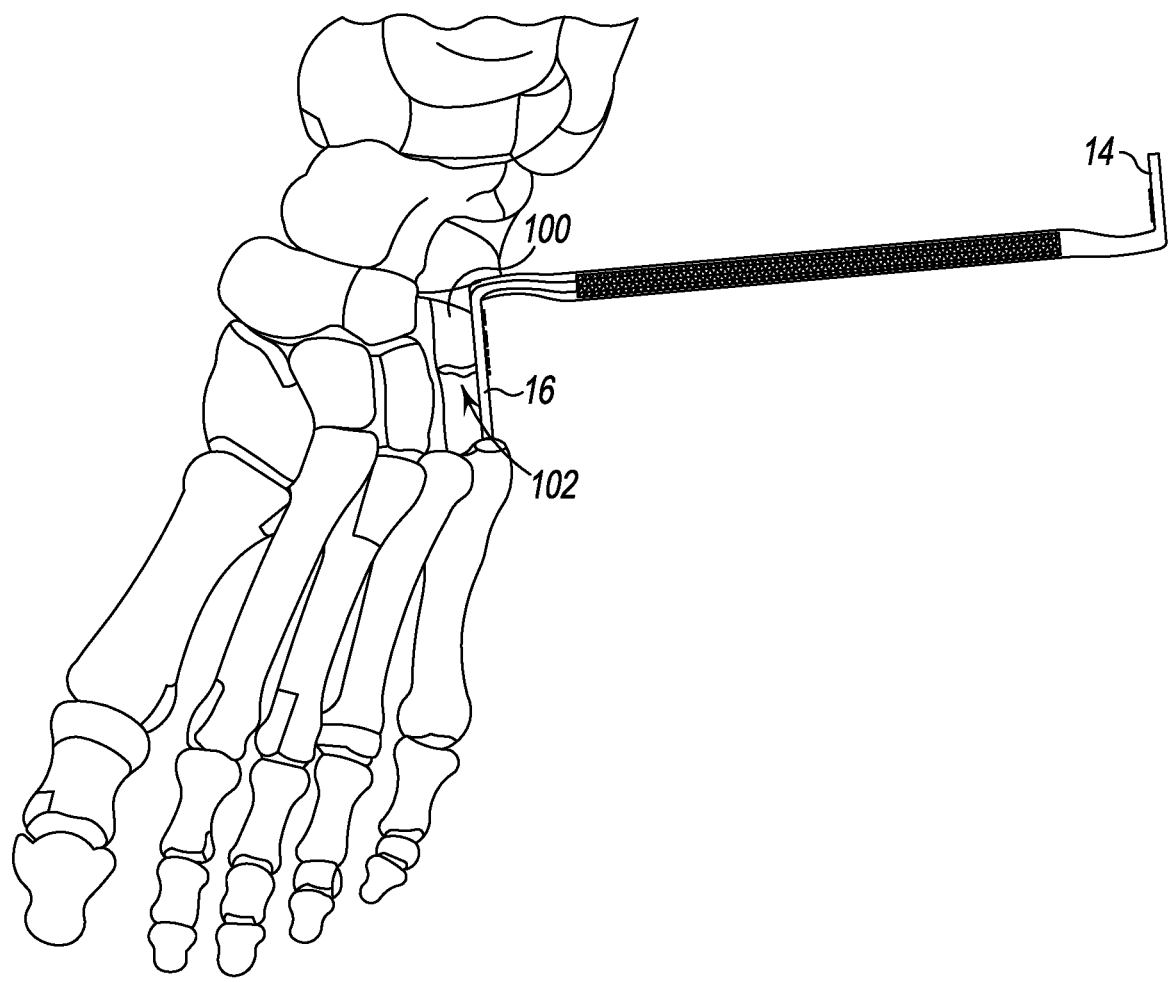
FIG. 6 is a perspective view of the surgical instrument of FIG. 1 and the patient's bone of FIG. 5 during a surgical procedure for implanting a fixation device.

Referring now to FIG. 6, the surgeon may insert one of the sizing plates 14, 16 of the instrument 10 into the incision 106. The surgeon may choose to begin with either of the plates 14, 16. For illustration purposes, FIG. 6 shows the sizing plate 16 being first positioned against the patient's bone 100 over the fracture 102. In that position, the surgeon may utilize the visible markings 18 on the plate 16 to identify one of the bone staple implants for implantation. To do so, the surgeon may align the plate 16 with the fracture 102 and determine the implant size appropriate to address the fracture 102. The surgeon may consider the size of the fracture, the size of the bone, the bone quality, and other relevant factors in selecting the bone staple implant.

Figure 7:
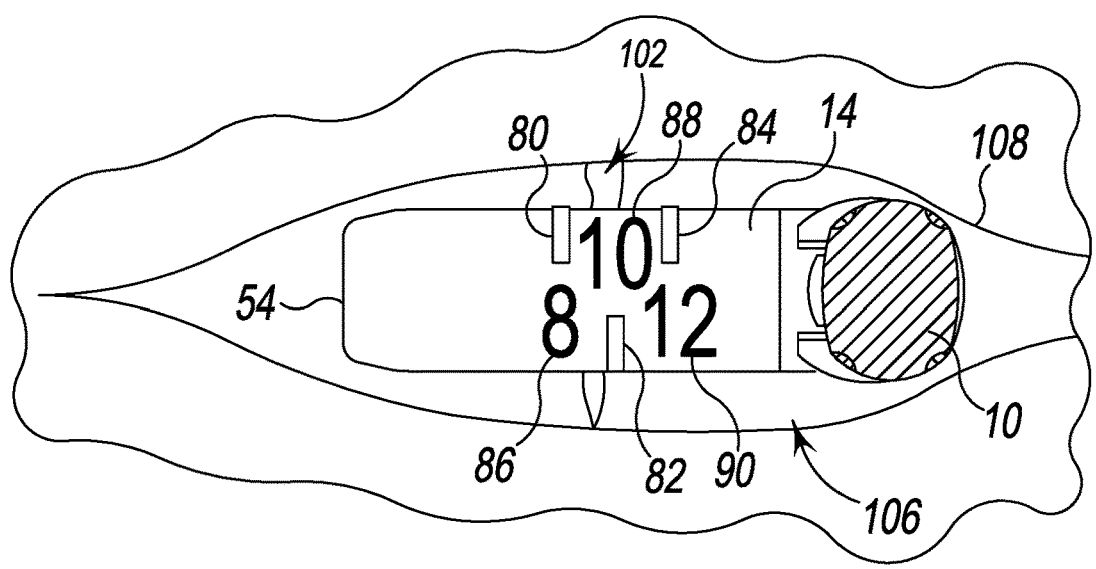
FIG. 7 is a plan view illustrating the surgical instrument in the position shown in FIG. 6.

If the surgeon determines that a staple implant smaller than those correlating to the sizing plate 16 is required, the surgeon may withdraw the sizing plate 16 from the incision 106, reverse the instrument 10, and insert the sizing plate 14 into the incision as shown in FIG. 7. The surgeon may align the plate 14 with the fracture 102 as shown in FIG. 7 and determine the implant size appropriate to address the fracture 102. In the illustrative embodiment, the surgeon may select the implant size identified by the tab 84 and the numerical indicator 90 (illustratively, size 12 mm).

Figure 8:
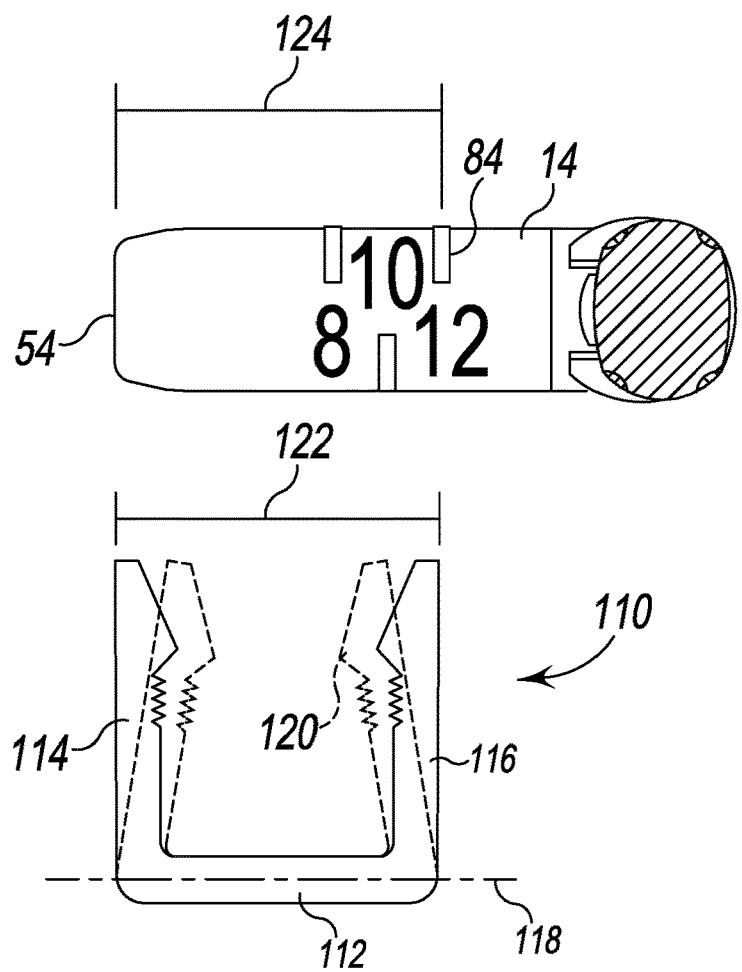
FIG. 8 is a plan view of the surgical instrument of FIG. 1 and a fixation device.

In the illustrative embodiment, each of the tabs 80, 82, 84, 200, 202, 204, and 206 identify a bone staple implant by its width. An exemplary bone staple implant 110 is shown in FIG. 8. The staple implant 110 includes the base 112 and a pair of arms 114, 116 extending outwardly from the base 112. The base 112 has a longitudinal axis 118 that extends traverse to the pair of arms 114, 116. The staple implant 110 is illustrative formed from nickel titanium or nitinol.

As illustrated in FIG. 8, the staple implant 110 is elastic and may be moved between a slack position 120 (shown in broken line) and an implantation position (shown in solid line). In the implantation position, a width 122 extending parallel to the axis 118 of the base 112 is defined between the tips of the arms 114, 116. This width 122 in the exemplary embodiment is equal to the third distance (labeled 124 in FIG. 8) that is defined between the tab 84 and the end wall 66 of the sizing plate 14.

Figure 9:
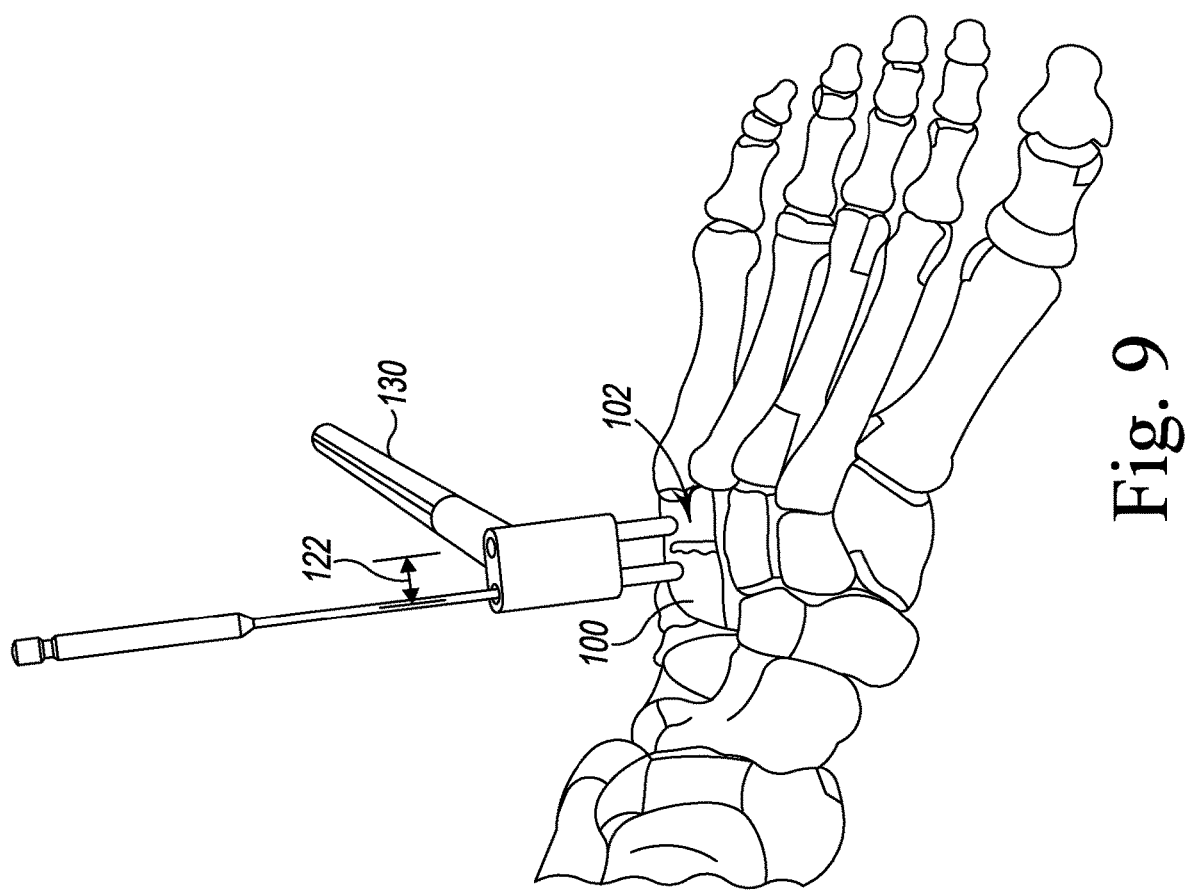
FIG. 9-10 are perspective views of the patient's bone of FIGS. 5-7 illustrating additional steps of the surgical procedure for implanting a fixation device.

Each staple implant may be included in a kit for use in the surgical procedure. The kit may include surgical instruments such as a drill guide 130 (see FIG. 9) and a surgical spreader assembly 132 (see FIG. 10). The kit may also include a drill, positioning pins, and other instruments necessary to prepare the bone. The staple implant may be included in a package or pouch containing one or more staple implants. In some embodiments, the instrument 10 may be included in the kit with or packaged separately for use with multiple kits (each kit including a different set of implant sizes). As shown in FIG. 9, the drill guide 130 includes a pair of guide bores 134, 136 sized to receive a drill to prepare the patient's bone 100 to receive the implant 110. The guide bores 134, 136 are spaced part by a distance 122 that equals the width 122 of the implant 110 (and hence the distance 124 of the sizing plate 14). It should be appreciated that each size of staple implant may require a different drill guide having a different set of guide bores.

Figure 10:
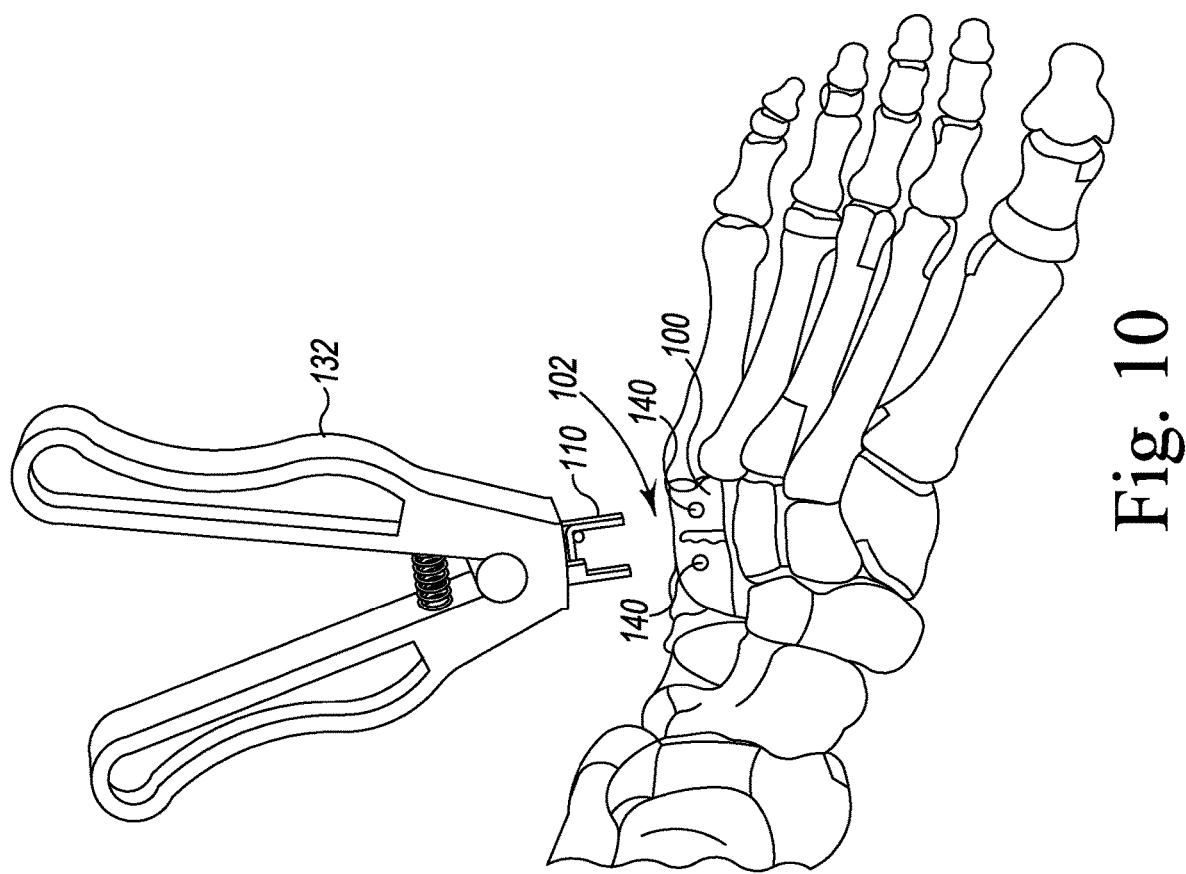

As shown in FIG. 10, the surgical spreader or inserter assembly 132 may be used to insert the implant 110 into the holes 140 formed in the patient's bone 100 on either side of the fracture 102 using the drill guide 130. An exemplary spreader assembly is shown and described in U.S. Patent App. Pub. No. 2016/0030039, which is expressly incorporated herein by reference.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An instrument system, comprising:
   a plurality of bone staple implants configured to be implanted into a patient's bone, each bone staple implant including a base extending along a longitudinal axis and a pair of arms extending outwardly from the base, the pair of arms being movable to an implantation position in which the arms of each bone staple implant are spaced apart when in the implantation position such that a width is defined between a tip of each arm,
   a surgical instrument including (i) an elongated body having a first longitudinal end and a second longitudinal end, (ii) a first sizing plate attached to and extending outwardly from the first longitudinal end, and (iii) a second sizing plate attached to and extending outwardly from the second longitudinal end,
   wherein the first sizing plate includes a first visible marking that identifies the width of a first bone staple implant of the plurality of bone staple implants, and
   wherein the second sizing plate includes a second visible marking that identifies the width of a second bone staple implant of the plurality of bone staple implants.

2. The instrument system of claim 1, wherein the first sizing plate extends from the first longitudinal end of the surgical instrument to a distal tip, and a first distance is defined between the distal tip and the first visible marking, the first distance being equal to the width of the first bone staple implant.

3. The instrument system of claim 2, wherein the second sizing plate extends from the second longitudinal end of the surgical instrument to a distal tip, and a second distance is defined between the distal tip of the second sizing plate and the second visible marking, the second distance being equal to the width of the second bone staple implant.

4. The instrument system of claim 1, wherein the first visible marking is one of a plurality of visible markings of the first sizing plate, each visible marking of the first sizing plate identifying the width of a different bone staple implant of the plurality of bone staple implants.

5. The instrument system of claim 1, wherein the second visible marking is one of a plurality of visible markings of the second sizing plate, each visible marking of the second sizing plate identifying the width of a different bone staple implant of the plurality of bone staple implants.

6. The instrument system of claim 1, wherein the first sizing plate extends away from the elongated body in a first direction, and the second sizing plate extends away from the elongated body in a second direction opposite the first direction.

7. The instrument system of claim 1, further comprising an inserter tool having a pair of jaws sized to engage the base of a bone staple implant of the plurality of bone staple implants.

8. The instrument system of claim 1, wherein the elongated body has a proximal surface that is positioned opposite the first sizing plate and is configured to retract the patient's tissue surrounding the patient's bone.

9. The instrument system of claim 8, wherein:
   the first sizing plate extends away from the elongated body along a longitudinal axis to a distal tip, and the first sizing plate has a plate thickness along an axis that is orthogonal to the longitudinal axis, and
   the proximal surface defines a thickness of the elongated body that is equal to the plate thickness.

10. The instrument system of claim 9, wherein the plate thickness of the first sizing plate is constant along its longitudinal axis between the elongated body and the distal tip.

11. The instrument system of claim 1, wherein the elongated body has a proximal surface that is positioned opposite the second sizing plate and is configured to retract the patient's tissue surrounding the patient's bone.

12. The instrument system of claim 11, wherein:
   the second sizing plate extends away from the elongated body along a longitudinal axis to a distal tip, and the second sizing plate has a plate thickness along an axis that is orthogonal to the longitudinal axis, and
   the proximal surface defines a thickness of the elongated body that is equal to the plate thickness.

13. The instrument system of claim 12, wherein the plate thickness of the second sizing plate is constant along its longitudinal axis between the elongated body and the distal tip.

14. A surgical instrument for use in sizing a bone staple implant for implantation into a patient's bone, comprising:
   an elongated body having a first longitudinal end and a second longitudinal end, the first longitudinal end and the second longitudinal end being configured to retract the patient's tissue surrounding the patient's bone,
   a first sizing plate attached to and extending outwardly from the first longitudinal end, and
   a second sizing plate attached to and extending outwardly from the second longitudinal end,
   wherein the first sizing plate includes a first visible marking that identifies a width of a first bone staple implant, and the second sizing plate includes a second visible marking that identifies a width of a second bone staple implant.

15. The surgical instrument of claim 14, wherein the first sizing plate extends from the first longitudinal end of the surgical instrument to a distal tip, and a first distance is defined between the distal tip and the first visible marking, the first distance being equal to the width of the first bone staple implant.

16. The surgical instrument of claim 15, wherein the second sizing plate extends from the second longitudinal end of the surgical instrument to a distal tip, and a second distance is defined between the distal tip of the second sizing plate and the second visible marking, the second distance being equal to the width of the second bone staple implant.

17. The surgical instrument of claim 14, wherein first visible marking is one of a plurality of visible markings of the first sizing plate, each visible marking of the first sizing plate identifying the width of a different bone staple implant of the plurality of bone staple implants.

18. The surgical instrument of claim 14, wherein second visible marking is one of a plurality of visible markings of the second sizing plate, each visible marking of the second sizing plate identifying the width of a different bone staple implant of the plurality of bone staple implants.

19. The surgical instrument of claim 14, wherein the first sizing plate extends away from the elongated body in a first direction, and the second sizing plate extends away from the elongated body in a second direction opposite the first direction.

\* \* \* \* \*